United States Patent
Washburn et al.

(10) Patent No.: US 8,090,168 B2
(45) Date of Patent: Jan. 3, 2012

(54) METHOD AND SYSTEM FOR VISUALIZING REGISTERED IMAGES

(75) Inventors: Michael Joseph Washburn, Bookfield, WI (US); Markus Wilhelm Marquart, Eching (DE); Todor Sheljaskow, Mercer Island, WA (US)

(73) Assignee: General Electric Company, Schenectady, NY (US)

( * ) Notice: Subject to any disclaimer, the term of this patent is extended or adjusted under 35 U.S.C. 154(b) by 1114 days.

(21) Appl. No.: 11/872,337

(22) Filed: Oct. 15, 2007

(65) Prior Publication Data

US 2009/0097723 A1   Apr. 16, 2009

(51) Int. Cl.
*A61B 5/05* (2006.01)
*G06K 9/00* (2006.01)
*G06K 9/34* (2006.01)

(52) U.S. Cl. ........ 382/128; 382/129; 382/130; 382/131; 382/232; 600/424; 600/425; 600/437; 600/439

(58) Field of Classification Search .................. 382/128, 382/129, 130, 131, 132, 232, 250; 600/424, 600/425, 437, 439
See application file for complete search history.

(56) References Cited

U.S. PATENT DOCUMENTS

| | | | | |
|---|---|---|---|---|
| 4,672,559 A | * | 6/1987 | Jansson et al. | 382/128 |
| 5,999,189 A | * | 12/1999 | Kajiya et al. | 382/232 |
| 6,052,492 A | * | 4/2000 | Bruckhaus | 382/284 |
| 6,282,327 B1 | * | 8/2001 | Betrisey et al. | 382/299 |
| 6,351,573 B1 | | 2/2002 | Schneider | |
| 6,393,145 B2 | * | 5/2002 | Betrisey et al. | 382/162 |
| 6,775,404 B1 | * | 8/2004 | Pagoulatos et al. | 382/154 |
| 7,024,054 B2 | * | 4/2006 | Cahill et al. | 382/294 |
| 7,035,371 B2 | | 4/2006 | Boese et al. | |
| 2001/0048764 A1 | * | 12/2001 | Betrisey et al. | 382/162 |
| 2003/0181809 A1 | * | 9/2003 | Hall et al. | 600/425 |
| 2004/0062439 A1 | * | 4/2004 | Cahill et al. | 382/173 |
| 2005/0100201 A1 | * | 5/2005 | Mayer et al. | 382/128 |
| 2005/0238218 A1 | * | 10/2005 | Nakamura | 382/128 |
| 2005/0281481 A1 | * | 12/2005 | Guendel | 382/276 |

OTHER PUBLICATIONS

Pagoulatos et al.: "Interactive 3-D Registration of Ultrasound and Magnetic Resonance Images Based on a Magnetic Position Sensor", published in IEEE Transactions on Information Technology in Biomedicine, vol. 3, No. 4, Dec. 1999.

* cited by examiner

*Primary Examiner* — David A Vanore

(57) ABSTRACT

A method for visualizing a registered image is presented. The method includes receiving a first image data set and at least one other image data set. Further, the method includes displaying at least a portion of the first image data set on a first portion of a display. Also, the method includes displaying at least a portion of the at least one other image data set on a second portion of the display. Additionally, the method includes selectively adjusting display of the at least a portion of the at least one other image data to provide a context to the first image data set. Systems and computer-readable medium that afford functionality of the type defined by this method is also contemplated in conjunction with the present technique.

25 Claims, 11 Drawing Sheets

METHOD AND SYSTEM FOR VISUALIZING REGISTERED IMAGES

BACKGROUND

The invention relates generally to imaging of an object, and more specifically to visualizing an image that is registered with a pre-acquired volume image data set.

Image registration finds wide application in medical imaging, video motion analysis, remote sensing, security and surveillance applications. Further, the process of finding the correspondence between the contents of the images is generally referred to as image registration. In other words, image registration typically entails finding a geometric transform that non-ambiguously links locations and orientations of the same objects or parts thereof in the different images. More particularly, image registration includes transforming the different sets of image data to a common coordinate space. The images may be obtained by different imaging devices or alternatively by the same imaging device but at different imaging sessions or time frames. As will be appreciated, in the field of medical imaging, there has been a steady increase in the number of imaging sessions or scans a patient undergoes. Images of a body part may be obtained temporally from the same imaging modality or system. Alternatively, in multi-modal imaging, images of the same body parts may be captured via use of different imaging modalities such as an X-ray imaging system, a magnetic resonance (MR) imaging system, a computed tomography (CT) imaging system, an ultrasound imaging system or a positron emission tomography (PET) imaging system.

In medical applications, registration of images is confronted by the challenges associated with patient movement. For example, due to either conscious or unconscious movement of the patient between two scans obtained either via the same imaging modality or otherwise, there exists an unpredictable change between the two scans. Unfortunately, this change in position leads to misalignment of the images. Additionally, patient position may vary depending on the imaging modalities used for multi-modal scanning. For example, a patient is generally positioned in the prone position (i.e., lying face down) for a magnetic resonance imaging (MRI) scanning session and may be in the supine position (i.e., lying face up) during a colon exam scanning session thereby creating inherent registration problems.

Volume-guided ultrasound is an application in which an ultrasound image may be registered to a previously acquired (pre-acquired) image volume. The pre-acquired volume data set may include a CT image data set, an MR image data set, a PET image data set, or an ultrasound image data set, for example. As will be appreciated, it may be desirable to simultaneously display the ultrasound image data and the corresponding slices or rendering from the pre-acquired volume image data set.

Previously conceived solutions to display the ultrasound image and the corresponding slices or rendering from the pre-acquired volume image data set include displaying the ultrasound image and a corresponding slice in a side-by-side configuration on a display of an imaging system. However, if the two images are displayed side-by-side then the screen size may limit the size of the displayed images. Alternatively, if the side-by-side display of the two images includes a larger display of the images, then partial clipping of the images may be required in order to accommodate the two images within a limited size of the display. Further, the pre-acquired image volume data set may include a substantially large volume of information. Consequently, if the two images are displayed in their entirety and in the same scale, then the displayed images are relatively small. Alternatively, the pre-acquired image volume image may be clipped off, however, the context of the currently displayed slice may not be easily understood.

There is therefore a need for a design of a method and system capable of efficiently visualizing a registered ultrasound image and a corresponding pre-acquired image volume data set in a side-by-side configuration. Further, there is also a need for a design of a method and system capable of visualizing an ultrasound image and a pre-acquired image volume data set that are overlaid on one another. In particular, there is a significant need for a design of a method and a system for visualizing registered images that enhances clinical workflow and facilitates superior diagnosis.

BRIEF DESCRIPTION

In accordance with aspects of the present technique, a method for visualizing a registered image is presented. The method includes receiving a first image data set and at least one other image data set. Further, the method includes displaying at least a portion of the first image data set on a first portion of a display. Also, the method includes displaying at least a portion of the at least one other image data set on a second portion of the display. Additionally, the method includes selectively adjusting display of the at least a portion of the at least one other image data to provide a context to the first image data set. Computer-readable medium that afford functionality of the type defined by this method is also contemplated in conjunction with the present technique.

In accordance with yet another aspect of the present technique, a method for visualizing a registered image is presented. The method includes receiving a first image data set and at least one other image data set, wherein the first image data set comprises an ultrasound image data set, and wherein the at least one other image data set comprises a pre-acquired medical image data set. Further, the method includes displaying at least a portion of the first image data set on a first portion of a display. In addition, the method includes displaying at least a portion of the at least one other image data set on a second portion of the display. The method also includes selectively adjusting display of the at least a portion of the at least one other image data to provide a context to the first image data set.

In accordance with further aspects of the present technique, a system is presented. The system includes at least one imaging system configured to obtain a first image data set and at least one other image data set. In addition, the system includes a processing sub-system operationally coupled to the at least one imaging system and comprising a visualization platform configured to display at least a portion of the first image data set on a first portion of a display, display at least a portion of the at least one other image data set on a second portion of the display, and selectively adjust display of the at least a portion of the at least one other image data to provide a context to the first image data set.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, an imaging system capable of superior visualization of a registered image, and methods of visualizing registered images are presented. Although, the exemplary embodiments illustrated hereinafter are described in the context of a medical imaging system, it will be appreciated that use of the imaging system capable of visualizing registered images in industrial applications are also contemplated in conjunction with the present technique. The industrial applications may include applications, such as, but not limited to, baggage scanning applications, and other security and surveillance applications.

Figure 1:
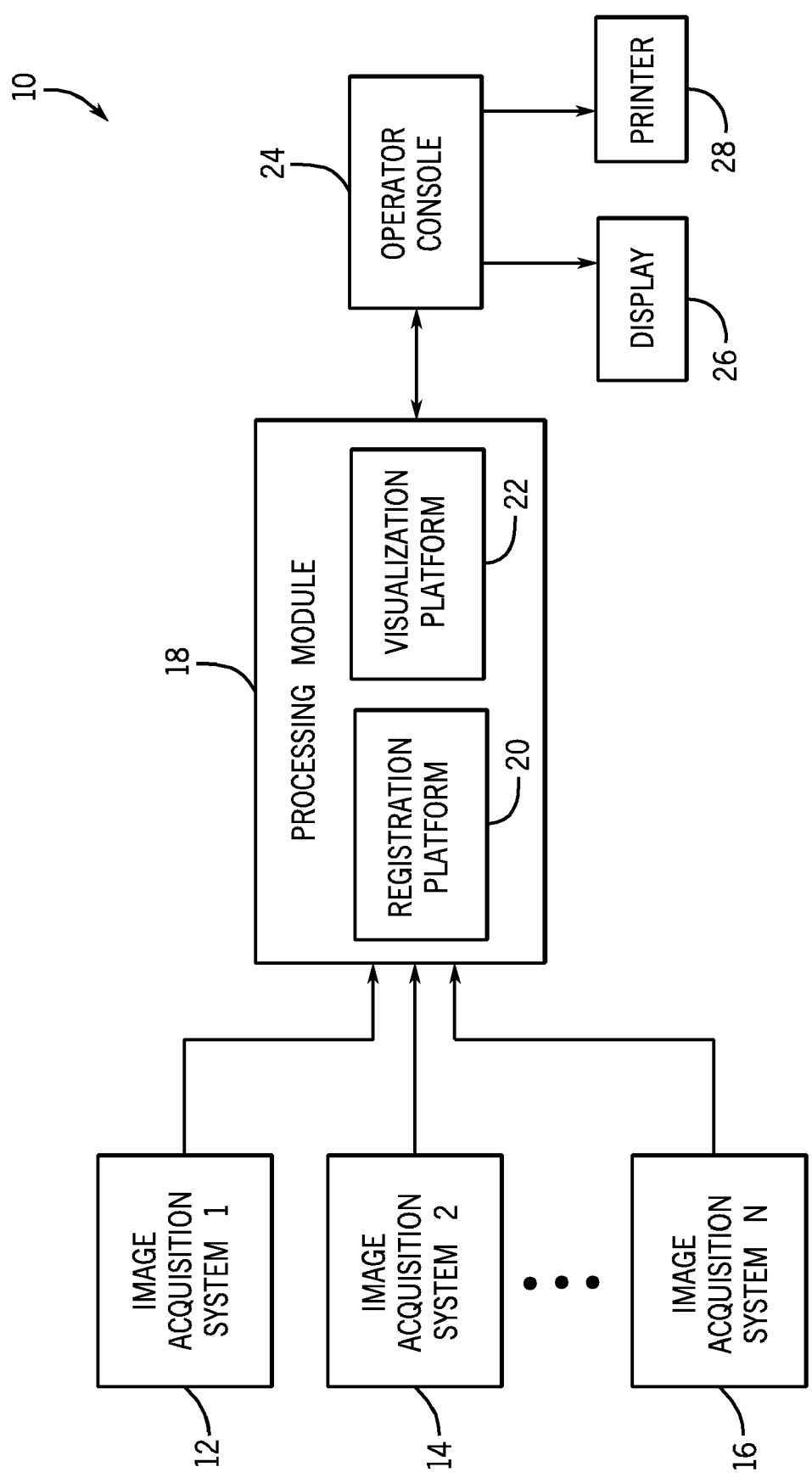
FIG. 1 is a block diagram of an exemplary diagnostic system, in accordance with aspects of the present technique.

FIG. 1 is a block diagram of an exemplary system 10 for use in imaging, in accordance with aspects of the present technique. More particularly, the system 10 may be configured to facilitate visualization of a registered image and a corresponding pre-acquired image volume. As will be appreciated by one skilled in the art, the figures are for illustrative purposes and are not drawn to scale. The system 10 may be configured to facilitate acquisition of image data from a patient (not shown in FIG. 1) via a plurality of image acquisition systems. In the illustrated embodiment of FIG. 1, the imaging system 10 is illustrated as including a first image acquisition system 12, a second image acquisition system 14 and an $N^{th}$ image acquisition system 16. It may be noted that the first image acquisition system 12 may be configured to obtain a first image data set representative of the patient under observation. In a similar fashion, the second image acquisition system 14 may be configured to facilitate acquisition of a second image data set associated with the same patient, while the $N^{th}$ image acquisition system 16 may be configured to facilitate acquisition of an $N^{th}$ image data set from the same patient.

In accordance with one aspect of the present technique, the diagnostic system 10 is representative of a multi-modality imaging system. In other words, a variety of image acquisition systems may be employed to obtain image data representative of the same patient. More particularly, in certain embodiments each of the first image acquisition system 12, the second image acquisition system 14 and the $N^{th}$ image acquisition system 16 may include a CT imaging system, a PET imaging system, an ultrasound imaging system, an X-ray imaging system, a MR imaging system, an optical imaging system or a combination thereof. For example, in one embodiment, the first image acquisition system 12 may include a CT imaging system, while the second image acquisition system 14 may include an ultrasound imaging system and the $N^{th}$ image acquisition system 16 may include a PET imaging system.

Further, in certain other embodiments, the imaging system 10 may include one image acquisition system, such as the first image acquisition system 12. In other words, the imaging system 10 may include a single modality imaging system. For example, the imaging system 10 may include only one image acquisition system 12, such as an ultrasound imaging system. In this embodiment, a plurality of images, such as a plurality of scans taken over a period of time, of the same patient may be obtained by the same image acquisition system 12.

The plurality of image data sets representative of the patient that has been obtained either by a single modality imaging system or by different image acquisition modalities may then be merged to obtain a combined image. As will be appreciated by those skilled in the art, imaging modalities such as PET imaging systems and single photon emission computed tomography (SPECT) imaging systems may be employed to obtain functional body images which provide physiological information, while imaging modalities such as CT imaging systems and MR imaging systems may be used to acquire structural images of the body that may serve as anatomic maps of the body. These different imaging techniques are known to provide image data sets with complementary and occasionally conflicting information regarding the body. It may be desirable to reliably coalesce these image data sets to facilitate generation of a composite, overlapping image that may include additional clinical information which may not be apparent in each of the individual image data sets. More particularly, the composite image facilitates clinicians to obtain information regarding shape, size and spatial relationship between anatomical structures and any pathology, if present.

Moreover, the plurality of image data sets obtained via a single imaging modality system may also be combined to generate a composite image. This composite image may aid clinicians in conducting follow-up studies in the patient or in a comparison of an image with normal uptake properties to an image with suspected abnormalities.

The plurality of acquired image data sets may be "registered" so that the image information associated with a region may be viewed from each image data set. These images may then be used to generate a composite display. Image registration techniques may be utilized to coalesce the plurality of image data sets obtained by the imaging system 10 via a processing module 18, in certain embodiments. In a presently contemplated configuration, the processing module 18 may include a registration platform 20, where the registration platform 20 may be configured to aid in the volume based registration of two or more image data sets. In the example illustrated in FIG. 1, the processing module 18 is operatively coupled to the image acquisition systems 12, 14, 16. As previously noted, image registration may be defined as a process of transforming the different image data sets into one common coordinate system. More particularly, the process of image registration involves finding one or more suitable transformations that may be employed to transform the image data sets under study to a common coordinate system. The transforms may include transforms, such as, but not limited to, rigid transforms, non-rigid transforms, or affine transforms. The rigid transforms may include, for example, translations, rotations or combinations thereof. Also, the non-rigid transforms may include finite element modeling (FEM), B-spline transforms, Daemon's (fluid flow based) methods, diffusion based methods, optic flow based methods, or level-set based methods, for example. It may be noted that when one of the image data sets is being continually updated, such as a real-time 2D or 3D ultrasound image data set, a position sensing system and/or image-based analysis may be used to maintain registration.

As described hereinabove, the registration platform 20 may be configured to facilitate the registration of the plurality of acquired image data sets to generate registered image data sets. Once registered, it may be desirable to visualize the registered image data sets on a display. There is therefore a need for a process that may be tailored to permit substantially superior visualization of the registered image data sets.

In accordance with aspects of the present technique, the processing module 18 may be configured to facilitate the display of the registered image data sets. Accordingly, in a presently contemplated configuration, the processing module 18 may include a visualization platform 22, where the visualization platform 22 may be configured to facilitate a substantially enhanced visualization of the registered image data sets on a display, for example. The working of the visualization platform 22 will be described in greater detail with reference to FIGS. 3-11.

The processing module 18 may be accessed and/or operated via an operator console 24. The operator console 24 may also be employed to facilitate the display of the registered image data sets generated by the processing module 18, such as on a display 26 and/or a printer 28. For example, an operator, such as a clinician, may use the operator console 24 to designate the manner in which the registered image and/or the pre-acquired image volume are visualized on the display 26.

Figure 2:
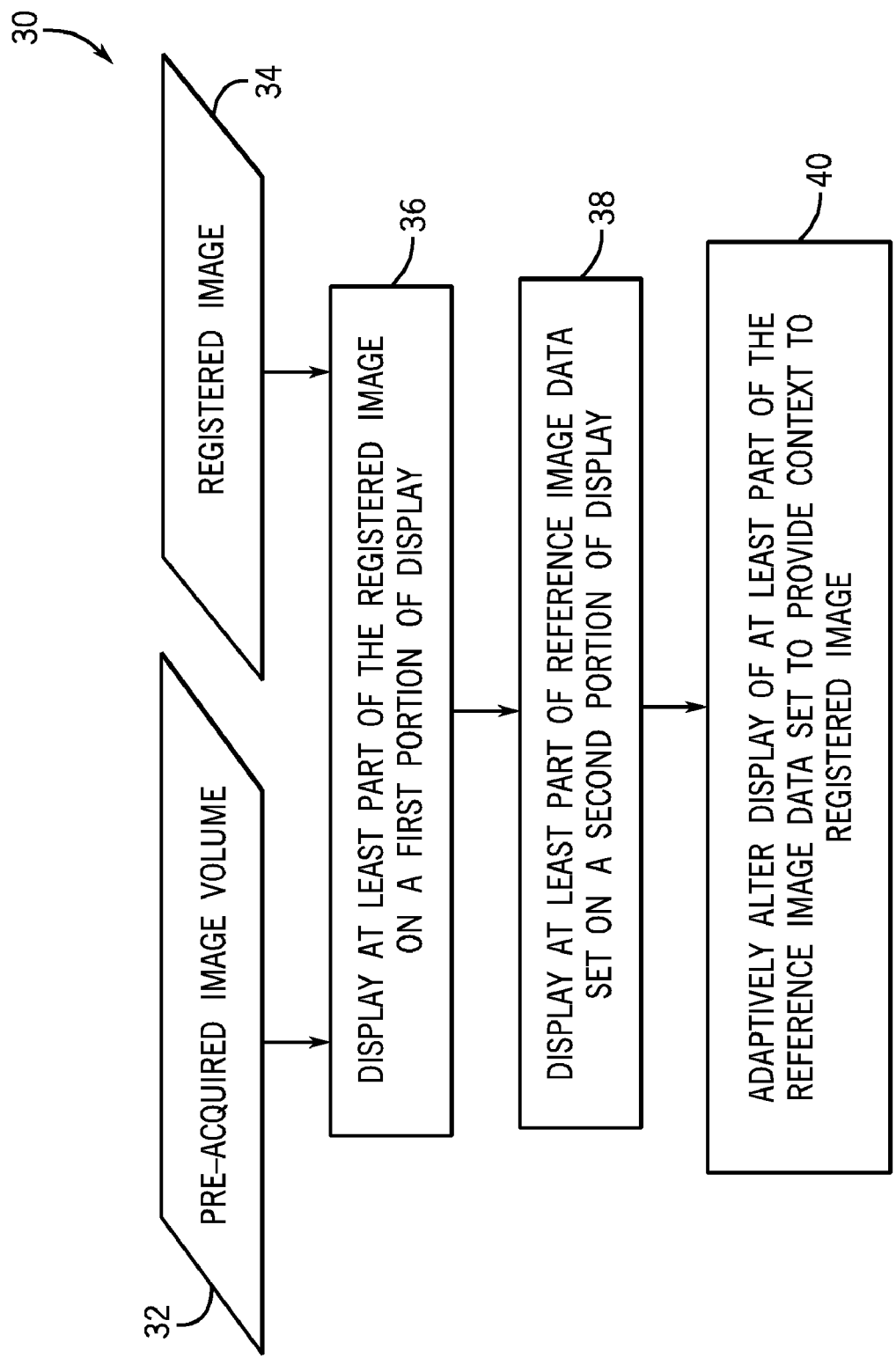
FIG. 2 is a flow chart illustrating an exemplary method of visualizing a registered image, in accordance with aspects of the present technique.

Turning now to FIG. 2, a schematic flow chart 30 representative of the operation of the diagnostic system 10 of FIG. 1, and more particularly of the visualization platform 22 in the processing module 18, is depicted. In other words, a method of visualizing a registered image using the system 10 (see FIG. 1) is depicted. In the example depicted in FIG. 2, reference numeral 32 may be representative of a first image data set acquired via an image acquisition system, such as the first image acquisition system 12 (see FIG. 1). Also, reference numeral 34 may be representative of a registered image. In one embodiment, the registered image 34 may include a registered ultrasound image.

In the present example, the first image data set 32 may be representative of a pre-acquired image volume, where the pre-acquired image volume may include image data representative of an anatomical region in the patient. Also, the first image data set 32 may be acquired via the first image acquisition system 12. Further, the first image acquisition system 12 may include a CT imaging system configured to obtain an image volume representative of the anatomical region of interest in the patient, for example. Accordingly, the first image data set 32 may include CT image data. More particularly, in one embodiment, the CT image volume 32 may include a series of parallel planar images (slices) that are in a standard orientation relative to the body of the patient. For example, an abdominal scan in CT is normally done with the patient lying on his back and the slices are parallel to each other and transverse to the patient. Further, the first image data set 32, acquired via the first image acquisition system 12 may be referred to as a "reference" image, where the reference image is the image that is maintained unchanged and thereby used as a reference. The reference image data set 32 may be representative of a pre-acquired image volume. It may be noted that the terms reference image, reference image data set, pre-acquired image volume, reference image volume, pre-acquired reference image volume, original image, source image and fixed image may be used interchangeably.

Additionally, the other acquired images to be mapped onto the reference image may be referred to as "floating" images. In other words, the floating image embodies the image that is geometrically transformed to spatially align with the reference image 32. It may also be noted that the terms floating image, moving image, sensed image and target image may be used interchangeably. Accordingly, a second image data set may be acquired via the second image acquisition system 14, for example. Further, in the present example, the second image acquisition system 14 may include an ultrasound imaging system configured to obtain an image representative of the anatomical region of interest, for example. Accordingly, the second image data set may include ultrasound image data. More particularly, in one embodiment, the ultrasound image data may include a two-dimensional (2D) planar image (slice). It may be noted that the second image data set may include a 2D ultrasound image that is acquired in real-time. This 2D ultrasound image may also be referred to as a "live" ultrasound image. Alternatively, the second image data set may include a multi-planar or 3D ultrasound images that are acquired in real-time.

Furthermore, this ultrasound image may be registered with the pre-acquired image volume 32 via use of the registration platform 20 (see FIG. 1). Registration techniques, such as, but not limited to rigid transformation, may be employed to register the ultrasound image with the reference image data set 32. In other words, the ultrasound image data set may be geometrically transformed to spatially align with the pre-acquired image volume 32. Consequent to processing by the registration platform 20, the registered ultrasound image 34 may be generated. Position sensor and/or image-based processing may be used to continually keep the image data sets registered as the position of the live ultrasound image is updated.

Subsequent to receiving the registered ultrasound image 34 and the corresponding pre-acquired image volume 32, it may be desirable to process the images 32, 34 to facilitate visualization on a display, such as the display 26 (see FIG. 1), thereby allowing a user, such as a clinician, to visualize the images 32, 34 and provide a diagnosis, for instance. In accordance with exemplary aspects of the present technique, a method for visualizing a registered image is presented. The method starts at step 36 where the registered floating ultrasound image 34 may be displayed on a first portion of the display 26. It may be noted that at step 36 the entire registered floating ultrasound image 34 or at least a portion of the registered floating ultrasound image 34 may be displayed on a first portion of the display 26. Subsequently, the pre-acquired reference image volume 32 may be displayed on a second portion of the display 26, as depicted by step 38. Here again, all of the pre-acquired reference image volume 32 or at least a portion of the pre-acquired reference image volume 32 may be displayed on the second portion of the display 26.

Figure 3:
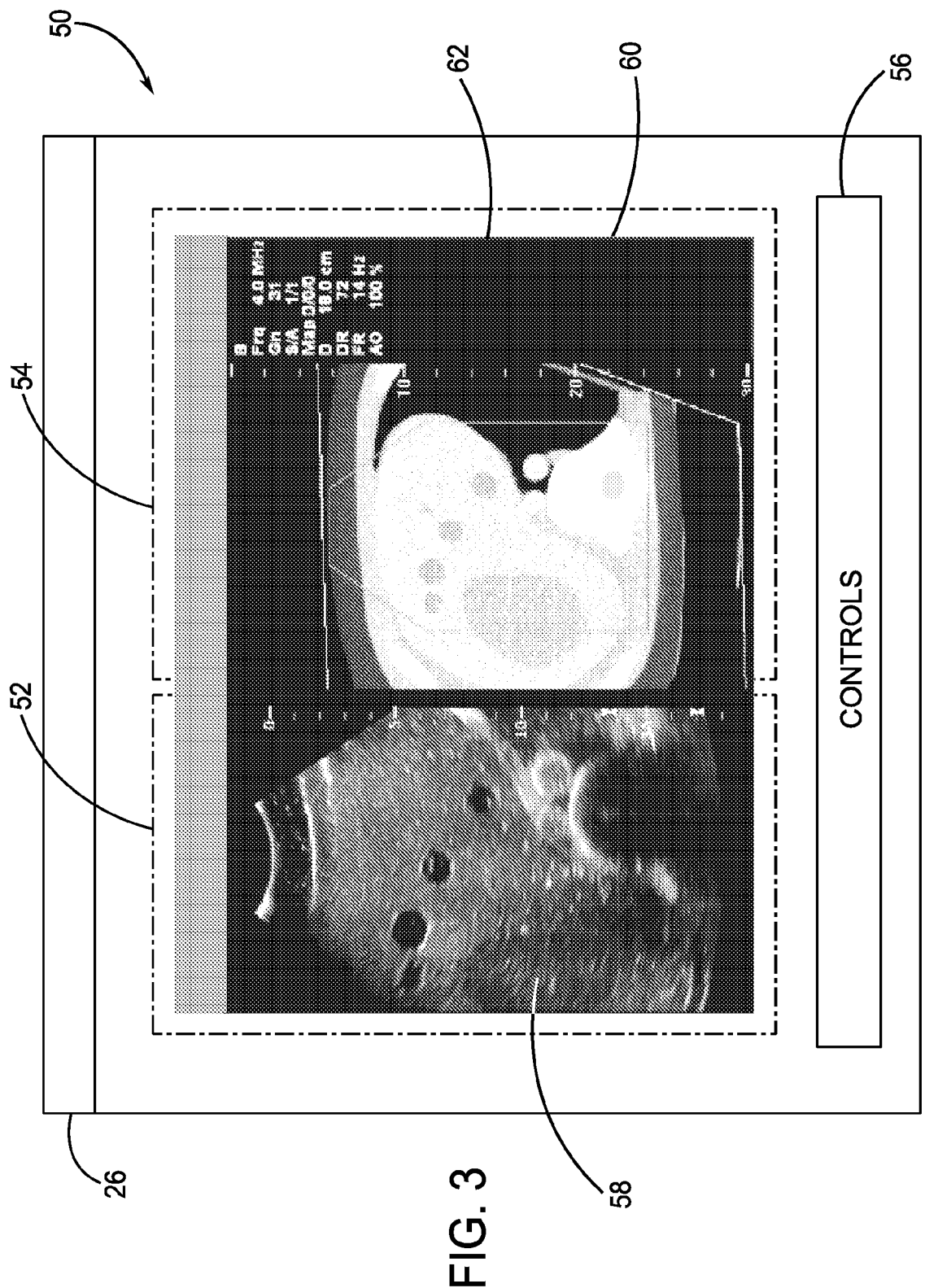
FIGS. 3-6 are front views of a display area of the exemplary diagnostic system of FIG. 1 depicting various methods of visualizing registered images in a side-by-side configuration, in accordance with aspects of the present technique.

Additionally, in one embodiment, the registered ultrasound image 34 and the pre-acquired reference image volume 32 may be visualized on the display 26 in a side-by-side configuration, as depicted in the example illustrated in FIG. 3. Accordingly, in the present example, the second portion of the display 26 may be adjacently disposed with reference to the first portion of the display 26.

Using the currently available techniques, the registered ultrasound image 34 may be displayed adjacent to the reference image volume 32, thereby allowing the clinician to view the two image data sets 32, 34 side by side, where the images 32, 34 are displayed in a substantially similar orientation and scale. More particularly, generally only a portion of the reference image volume 32 corresponding to the ultrasound image 34 is displayed, thereby disadvantageously resulting in a loss of context for the ultrasound image 34 in reference to the reference image volume 32. For example, the pre-acquired image volume 32 may include CT image data, where the CT image data is generally representative of images of a cross-section of the body of the patient. One the other hand, the ultrasound image 34 may include ultrasound data that is acquired via an ultrasound transducer as the transducer is moved along the body of the patient. Hence, the CT image data in the pre-acquired image volume 32 may provide a relatively larger context to the ultrasound image 34. However, if only a portion of the CT image data in the pre-acquired image volume 32 corresponding to the ultrasound image 34 is visualized along with the ultrasound image 34 such that both the images 32, 34 are displayed in a substantially similar scale, then this context may be lost.

The shortcomings of the currently available techniques may be advantageously overcome by allowing the clinician to selectively alter the display of the reference image data set 32 on the second portion of the display 26. In other words, in accordance with exemplary aspects of the present technique, the clinician may be allowed to modify the scale of the reference image volume 32 such that the altered reference image volume is configured to provide a substantially larger context for the ultrasound image 34, as depicted by step 40. By way of example, in one embodiment, the clinician may be allowed to zoom out on the pre-acquired reference image volume 32 such that a side-by-side comparison between the ultrasound image 34 and the pre-acquired image volume 32 is substantially similar. More particularly, the system 10 (see FIG. 1) may be configured to allow the clinician to selectively alter the display of at least a portion of the pre-acquired image volume 32 to provide an enhanced context to the registered ultrasound image 34.

In accordance with further aspects of the present technique, the system 10 may also be configured to provide a user-defined amount of additional image data to give a context to the ultrasound image 34. In other words, using the system 10, the clinician may incorporate additional information on the reference image data set 32 to provide a perspective to the ultrasound image 34 with respect to the reference image data set 32 displayed on the second portion of the display 26 of the system 10, for example.

The method of visualizing the registered image 34 depicted in steps 36-40 of FIG. 2 may be better understood with reference to FIGS. 3-11. More particularly, FIGS. 3-11 present a variety of methods for selectively altering the visualization of the reference image volume 32 on the second portion of the display 26.

Turning now to FIG. 3, a front view 50 of a display, such as the display 26 of FIG. 1, is illustrated. More particularly, a method of visualizing a registered ultrasound image, in accordance with aspects of the present technique, is depicted. Reference numeral 52 may be representative of a first portion of the display 26, while a second portion of the display 26 may generally be represented by reference numeral 54. Also, reference numeral 56 may be indicative of a controls portion of the display 26. As previously noted, a registered ultrasound image 58 may be displayed on the first portion 52 of the display 26. It may be noted that the registered ultrasound image 58 may be representative of the ultrasound image 34 (see FIG. 2). Similarly, a pre-acquired reference image volume 60 may be visualized on the second portion 54 of the display 26. Here again, the pre-acquired reference image volume 60 may be indicative of the reference image volume 32 (see FIG. 2). It may be noted that in the example depicted in FIG. 3, the registered ultrasound image 58 and the reference image volume 60 are displayed in a side-by-side configuration.

Further, in the example presented in FIG. 3, providing a substantially larger context for the ultrasound image 58 via use of the pre-acquired image volume 60 may circumvent disadvantages associated with the presently available techniques. More particularly, in the present example, the system 10 (see FIG. 1) may be configured to provide the clinician an ability to zoom out on the pre-acquired volume data set 60 such that a side-by-side comparison between the registered ultrasound image 58 and the pre-acquired image volume 60 is substantially similar. In other words, the pre-acquired reference image volume 60 may now be visualized in a relatively reduced scale in comparison to the ultrasound image 58. More particularly, the registered ultrasound image 58 may now have a zoom factor that is relatively different from a zoom factor of the pre-acquired reference image volume 60.

In accordance with further aspects of the present technique, a user-defined amount of additional image data may be incorporated to provide a context to the ultrasound image 58 via use of the pre-acquired image volume 60. In the present example depicted in FIG. 3, the user-defined context may be provided via incorporation of a graphical outline 62 of the registered ultrasound image 58 on the pre-acquired image volume 60 displayed on the second portion 54 of the display 26. The outline 62 may be representative of an outline of the registered ultrasound image 58 displayed on the first portion 52 of the display 26, in one embodiment. By implementing the display of the registered ultrasound image 58 and the modified pre-acquired image volume 60 as described hereinabove, any information in the pre-acquired reference image volume 60 that lies outside of the graphical outline 62 may advantageously be employed to provide an anatomical context to the ultrasound image 58. Alternatively, instead of using the graphical outline 62, an intensity of an area outside the corresponding ultrasound area may be reduced to provide an anatomical context to the ultrasound image 34.

Figure 4:
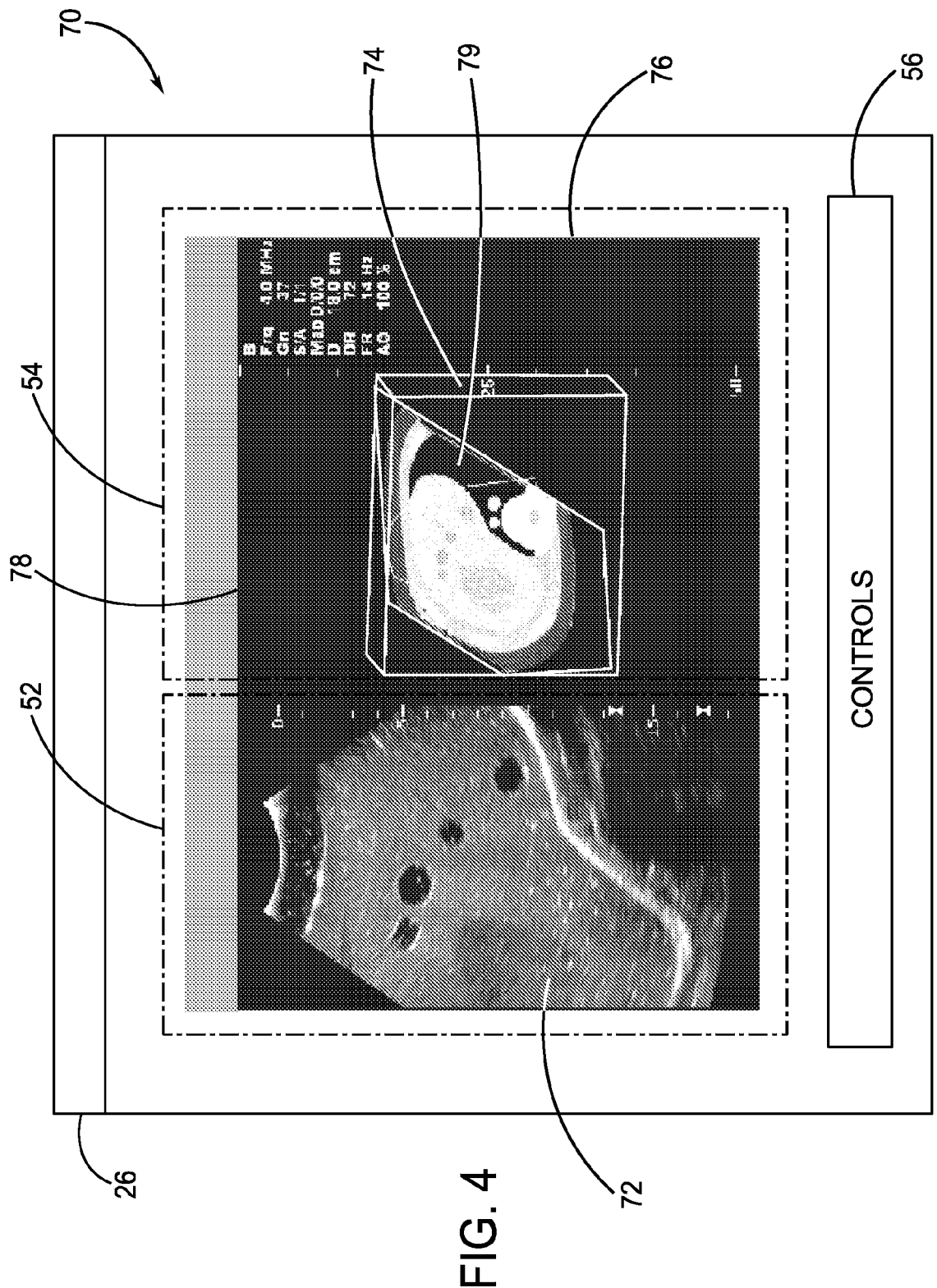

Referring now to FIG. 4, a front view 70 of a display, such as the display 26 of FIG. 1, is illustrated. In other words, another method of visualizing a registered ultrasound image, in accordance with further aspects of the present technique, is depicted. Reference numeral 72 may be representative of a registered ultrasound image displayed on the first portion 52 of the display 26. In certain embodiments, the ultrasound image 72 may be representative of the registered ultrasound image 34 (see FIG. 2). In the example illustrated in FIG. 4, the system 10 (see FIG. 1) may be configured to allow the clinician to view the entire context of a pre-acquired reference image volume 74. Here again, the pre-acquired image volume 74 may be representative of the pre-acquired image volume 32 (see FIG. 2). More particularly, the pre-acquired reference image volume 74 may be visualized in a predetermined orientation. The predetermined orientation may include a substantially fixed orientation, in one embodiment. It may be noted that, in a presently contemplated configuration, reference numeral 78 may be indicative of an outline of the pre-acquired image volume 74.

Furthermore, an image plane in the pre-acquired reference image volume that substantially matches the registered ultrasound image 72 may be extracted. Reference numeral 76 may be representative of the matching image plane in the pre-acquired reference image volume 74. Additionally, in accordance with further aspects of the present technique, the matching image plane 76 may be displayed on the second portion 54 of the display 26. In the example illustrated in FIG. 4, the matching image plane 76 is shown in its position relative to the overall pre-acquired image volume 74. In other words, the matching image plan 76 may be depicted at an angle within the outline 78 of the pre-acquired image volume 74, in accordance with aspects of the present technique. Consequently, in FIG. 4, the ultrasound image 72 and the corresponding matching image plane 76 that is currently displayed in its position within the pre-acquired image volume 74 may be displayed in a side-by-side display configuration. Also, as previously described with reference to FIG. 3, a graphical outline 79 representative of the ultrasound image 72 may be superimposed on the matching image plane 76 in the pre-acquired image volume 74 to provide an additional context to the ultrasound image 72. Alternatively, instead of using the graphical outline 79, an intensity of the area outside the corresponding ultrasound area may be reduced to provide additional context to the ultrasound image 72.

As will be appreciated, an ultrasound transducer (not shown in FIG. 4) may be employed to facilitate acquisition of ultrasound image data representative of an anatomical region of interest, where the acquired ultrasound image may be displayed as the ultrasound image 72 on the first portion 52 of the display 26. It may be noted that in the present example depicted in FIG. 4 the ultrasound transducer is oriented in a plane of the matching image plane 76 in the pre-acquired image volume 74. Moreover, if the ultrasound transducer is rotated about the Y-axis by about 180 degrees, then an orientation of the pre-acquired volume image data set may be reversed to facilitate maintaining a substantially consistent orientation between the ultrasound image 72 and the matching image plane 76 in the pre-acquired image volume 74. Further, visualizing the entire pre-acquired image volume 74 on the second portion 54 of the display 26 may result in a relatively small display size of the pre-acquired image volume 74. Accordingly, the system 10 may be configured to provide the clinician with a user adjustable zoom factor, where the user adjustable zoom factor may be used to trade off image size for anatomical context.

Implementing the display of the ultrasound image 72, the matching image plane 76, and the pre-acquired image volume 74 as described with reference to FIG. 4 advantageously allows the clinician to visualize the ultrasound image 72 in reference to the entire context of the pre-acquired image volume 74, thereby providing a substantially enhanced anatomical context. More particularly, image data that lies outside of the graphical outline 79 provides an additional context to the ultrasound image 72. Additionally, the clinician may visualize the entire pre-acquired image volume 74. Further, the user-adjustable zoom-factor allows the clinician to adjust a field of view of the display of the pre-acquired image volume 74 on the second portion 54 of the display 26, thereby providing a substantially enhanced anatomical context.

Figure 5:
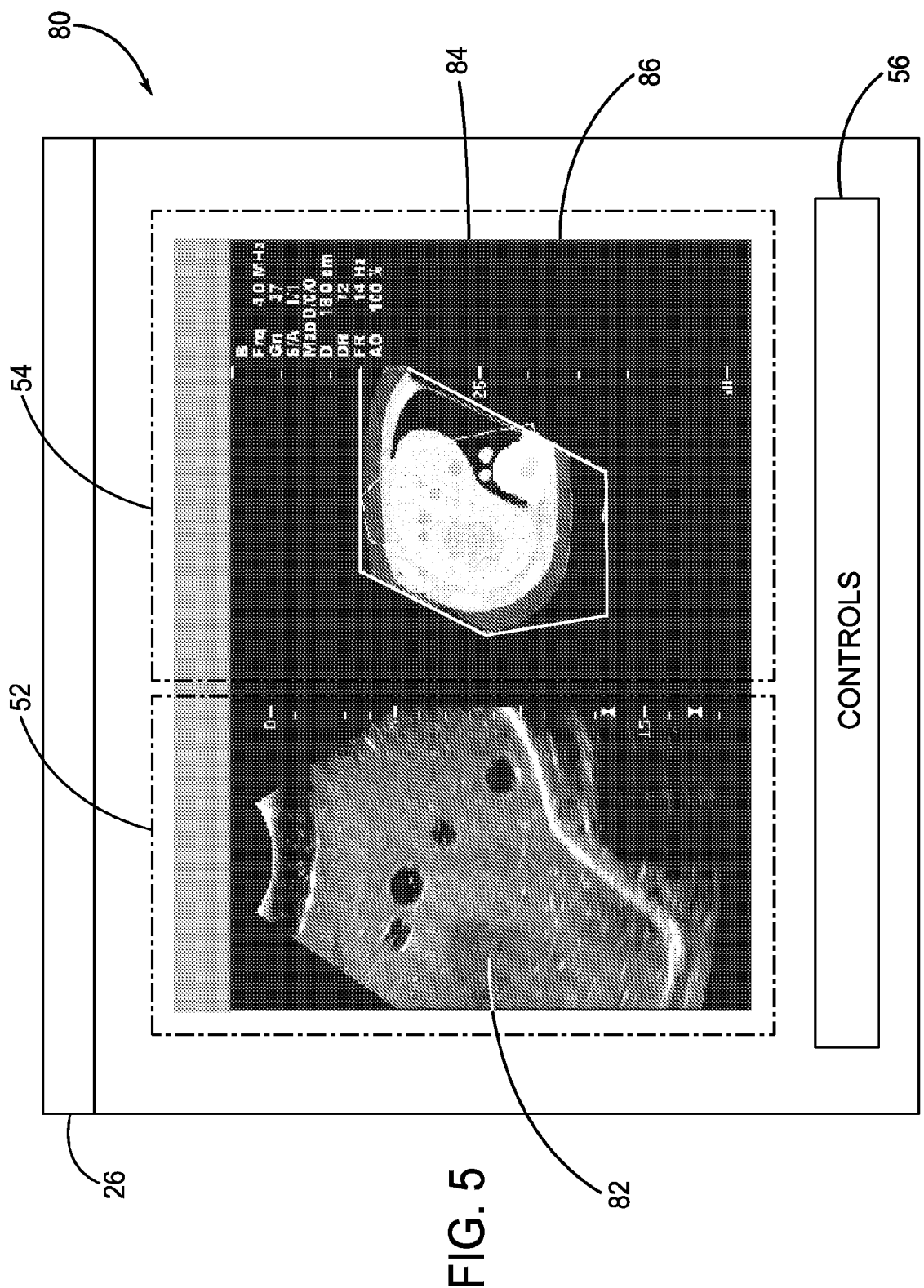

FIG. 5 illustrates a front view 80 of a display, such as the display 26 of FIG. 1. More particularly, yet another method of visualizing a registered ultrasound image, in accordance with further aspects of the present technique, is depicted. In a presently contemplated configuration, at least a portion of the pre-acquired image volume may be visualized in a predetermined orientation, where the predetermined orientation does not include a substantially fixed orientation. In other words, in the present example, a registered ultrasound image 82 may be displayed in a side-by-side configuration along with a matching image slice in the corresponding pre-acquired image volume. Here again, as previously described with reference to FIG. 4, the system 10 (see FIG. 1) may be configured to extract an image plane in the pre-acquired reference image volume that substantially matches the registered ultrasound image 82. This matching image plane in the pre-acquired reference image volume may generally be represented by reference numeral 84. In addition, in accordance with further aspects of the present technique, the matching image plane 84 may be displayed on the second portion 54 of the display 26. Further, in the example illustrated in FIG. 5, the matching image plane 84 may be oriented such that the matching image plane 84 is substantially parallel to the display 26. Consequently, in FIG. 5, the ultrasound image 82 may be visualized in a side-by-side display configuration along with the corresponding matching image plane 84 in the pre-acquired image volume. Also, as previously described with reference to FIGS. 3-4, an outline 86 representative of the registered ultrasound image 82 may be superimposed on the matching image plane 84 to provide an additional context to the ultrasound image 82 in the pre-acquired image volume. Alternatively, instead of using the graphical outline 86, an intensity of the area outside the corresponding ultrasound area may be reduced to provide an enhanced anatomical context to the ultrasound image 82.

In accordance with further aspects of the present technique, a plurality of image planes from the pre-acquired image volume may be employed to provide an anatomical context to a registered ultrasound image. As will be appreciated, an ultrasound image may include a 2D image, while a pre-acquired image volume includes a three-dimensional (3D) volume.

Accordingly, in one embodiment, the registered ultrasound image may be simultaneously displayed along with one or more image planes from the corresponding pre-acquired reference image volume that intersect the ultrasound image. Furthermore, in certain embodiments, the center of the ultrasound image may be selected as a point of intersection between the ultrasound image and the pre-acquired image volume. Subsequently, one or more intersecting planes in the pre-acquired image volume that pass through the point of intersection may be selected to provide anatomical context to the ultrasound image. Alternatively, the clinician may select a point of intersection on the ultrasound image and accordingly select one or more image planes in the pre-acquired image volume that pass through the user-selected point of intersection. In accordance with further aspects of the present technique, one or more image planes in the pre-acquired image volume that are substantially parallel to the ultrasound image may be simultaneously displayed along with the ultrasound image. In addition, the ultrasound image may be displayed in a side-by-side configuration with a volume rendering of all or part of the pre-acquired image volume.

Figure 6:
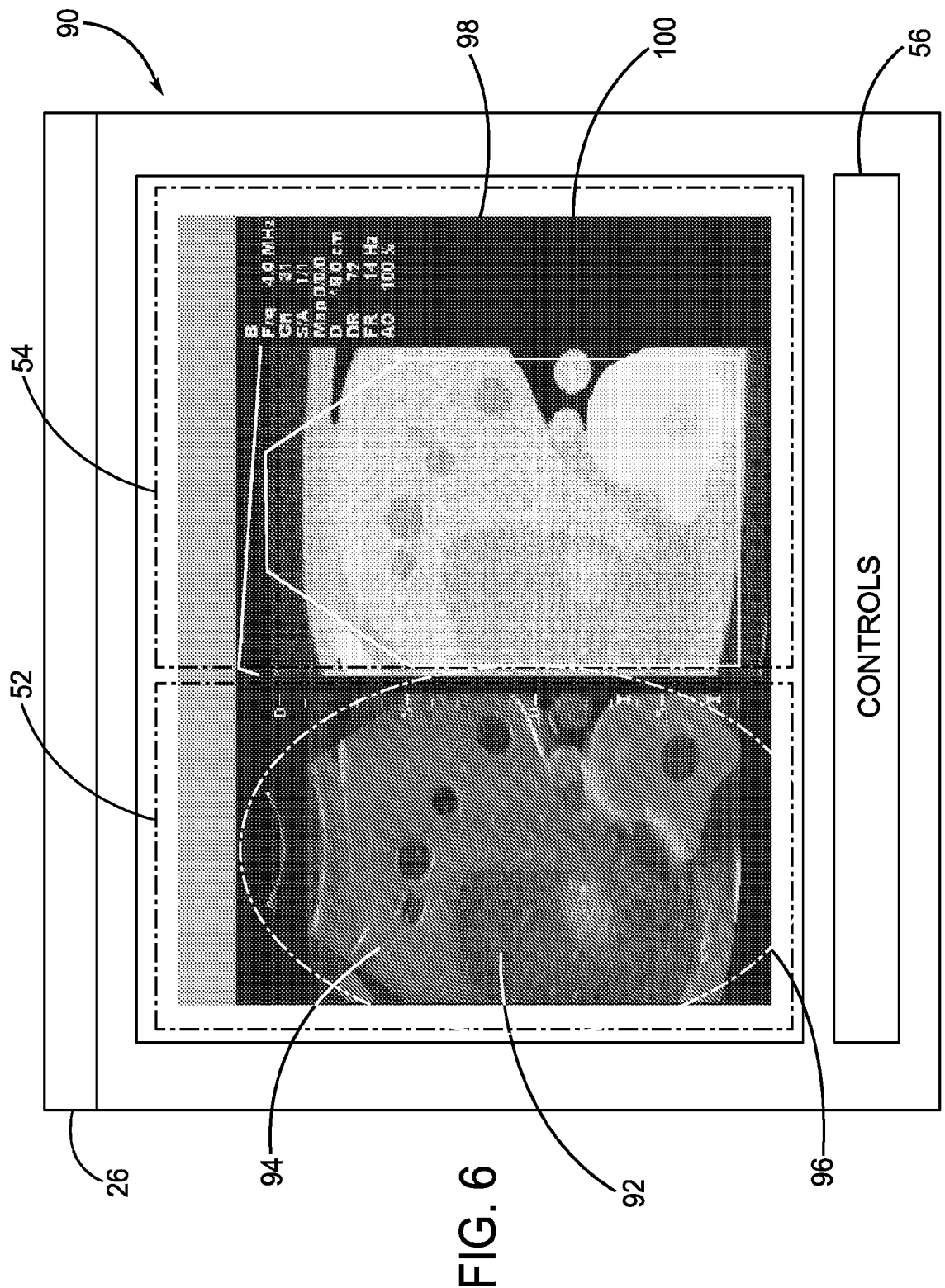

Turning now to FIG. 6, a front view 90 of a display, such as the display 26 (see FIG. 1), is illustrated. More particularly, yet another method of visualizing a registered ultrasound image, in accordance with further aspects of the present technique, is depicted. Reference numeral 92 may be representative of a registered ultrasound image, while a pre-acquired image volume may generally be represented by reference numeral 98. In a presently contemplated configuration, a matching image slice that substantially matches the ultrasound image 92 may be extracted from the pre-acquired image volume 98. The extracted matching image slice and the ultrasound image 92 may be combined to generate a composite image. More particularly, the matching image slice may be colorized. In other words, the matching image slice may be mapped from a standard gray representation. In the example illustrated in FIG. 6, reference numeral 94 may be representative of a colorized matching image slice in the pre-acquired image volume 98. Subsequently, the colorized matching image slice 94 may be combined with the gray ultrasound image 92 to create a composite or overlay image 96. Alternatively, the ultrasound image 92 may be colorized and combined with the pre-acquired image volume 98, where the pre-acquired image volume 98 includes a grayscale image.

Furthermore, information associated with the matching image slice 94 may also be extracted. The extracted information may also be combined with the ultrasound image 92 to generate a composite image. Subsequently, the composite image so generated may be displayed on the first portion 52 of the display 26, for example.

These composite images may then be visualized on the display 26 to provide a substantially superior anatomical context to the ultrasound image 92. Further, in a presently contemplated configuration, this composite image 96 may be displayed on the first portion 52 of the display 26. Also, as previously described with reference to FIGS. 3-5, an outline 100 representative of the ultrasound image 92 may be superimposed on the pre-acquired image volume 98 to provide an additional context to the ultrasound image 92 in the pre-acquired image volume 98.

In accordance with further aspects of the present technique, another method of visualizing a registered ultrasound image is presented. As will be appreciated, in normal ultrasound scanning, the B-mode or grayscale image is an anatomical representation. Additionally, ultrasound has the ability to generate vascular flow information using Color Doppler, Power Doppler, Contrast, Pulsatile Flow Detection and Colorize B Flow (not shown in FIG. 6). This flow information may be displayed as an overlay on the ultrasound B-mode image 92. In volume-guided ultrasound, this color overlay may be overlaid on the ultrasound image 92, the corresponding matching slice in the pre-acquired volume image slice 98, or both. In addition, a biopsy graphic overlay (not shown in FIG. 6) may be combined with the ultrasound image 92, the pre-acquired image volume 98, or both.

As will be appreciated, ultrasound image data representative of an anatomical region of interest may also be acquired via use of a volume transducer or a multi-planar transducer. Consequently, multiple ultrasound planes simultaneously representative of the anatomical region of interest may be obtained. Accordingly, the multiple ultrasound images so obtained may be displayed on the first portion 52 of the display 26, while the corresponding matching slices from the pre-acquired image volume 98 may be displayed on the second portion 54 of the display 26, for example. It may be noted that the various techniques described hereinabove with reference to FIGS. 3-6, may also be extended to these multiple image cases, in accordance with aspects of the present technique.

Further, a volume ultrasound transducer may also be used to generate a volumetric view of the ultrasound image data representative of an anatomical region of interest. The volumetric view may include a rendering, for example. In accordance with yet another aspect of the present technique, the rendering so generated may be displayed in a side-by-side configuration with a rendering of a corresponding pre-acquired image volume, where the pre-acquired image volume is representative of the same anatomical region of interest. Alternatively, the rendering of the ultrasound image may be displayed in a side-by-side configuration with one or more image planes from the pre-acquired image volume. In other words, the rendering of the ultrasound image may be displayed on the first portion 52 of the display 26, while the corresponding one or more planes from the pre-acquired image volume may be displayed on the second portion 54 of the display 26.

Typically, two or more image planes representative of an anatomical region of interest may be simultaneously acquired via a multi-planar transducer or volume transducer. In certain embodiments, these image planes may include two perpendicular planes, such as an A-plane and a B-plane. Also, in certain other embodiments, it may be desirable to obtain a third orthogonal plane, such as a C-plane, where the C-plane is generally substantially parallel to a face of the transducer. However, the acquisition of the C-plane may not be practical for real-time scanning as the acquisition of the C-plane may include the acquisition of an entire volume of information to capture desired data. This shortcoming may advantageously be circumvented in accordance with aspects of the present technique. Accordingly, in one embodiment, the ultrasound transducer may be configured to acquire and display the A-plane and the B-plane. The C-plane may be obtained from the corresponding pre-acquired image volume data set and displayed along with the A-plane and B-plane of the ultrasound image data. Also, the system 10 (see FIG. 1) may be configured to allow the clinician to specify the depth of the C-plane.

Furthermore, in certain conditions, a substantially enhanced image quality may be desired. Accordingly, the system 10 (see FIG. 1) may also be configured to allow the clinician to obtain and display any of the A-plane, the B-plane, or the C-plane from the pre-acquired volume data set to provide the desired image quality. By implementing the visualization of the ultrasound image and the pre-acquired image volume as described hereinabove, image quality may be enhanced especially if the reference volume data set is pre-acquired with the same ultrasound probe from a different angle to avoid shadowing or other imaging artifacts.

As described hereinabove with reference to FIGS. 3-6, a graphical indicator and/or image-embedded indicators of the area that corresponds directly to ultrasound image area may be placed on the pre-acquired image volume, thereby providing a superior anatomical context to the registered ultrasound image and facilitating enhanced visualization. In the examples of FIGS. 3-6, an example of a graphical indication includes a graphical outline of the ultrasound image area incorporated on the image representative of the pre-acquired image volume. These image-embedded indications may advantageously be employed to enhance the visualization of the ultrasound image and the pre-acquired image volume. Accordingly, a variety of image-embedded indications are provided, in accordance with aspects of the present technique.

By way of example, the image-embedded indication may include representing image data in the pre-acquired image volume corresponding to the ultrasound image in a first color, while other image data in the pre-acquired image volume may be represented in a second color, where the second color is different from the first color. Alternatively, the image data in the pre-acquired volume corresponding to the ultrasound image may be represented by a first shade of a color, while other image data in the pre-acquired image volume may be represented in a second shade of the same color, where the second shade is different from the first shade. According to further aspects of the present technique, a method of visualizing the registered image may include transparently overlaying the ultrasound image data onto a corresponding part of the pre-acquired image volume.

Further, simultaneous overlay viewing typically combines the ultrasound 2D image with a corresponding matching image slice in the pre-acquired image volume. For example, the simultaneous overlay may be generated by colorizing one of the ultrasound image or the pre-acquired image volume. In addition, some transparency may be employed to allow the clinician to view both image data sets. Alternatively, a combining algorithm may be employed to combine the two images at each point.

Presently available techniques typically combine the overlay viewing with simultaneous side-by-side viewing of the pre-acquired image volume, thereby providing a combined image on a first portion of a display and the uncombined pre-acquired volume slice on a second portion of the display. Also, in certain cases, the ultrasound 2D image slice may cover a relatively smaller area in comparison to an area covered by the corresponding matching image slice in the pre-acquired image volume. In accordance with aspects of the present technique, while combining the ultrasound image with the corresponding matching image slice from the pre-acquired image volume, a relatively larger slice area may be used, thereby providing a substantially greater anatomical context for the ultrasound image.

Figure 7:
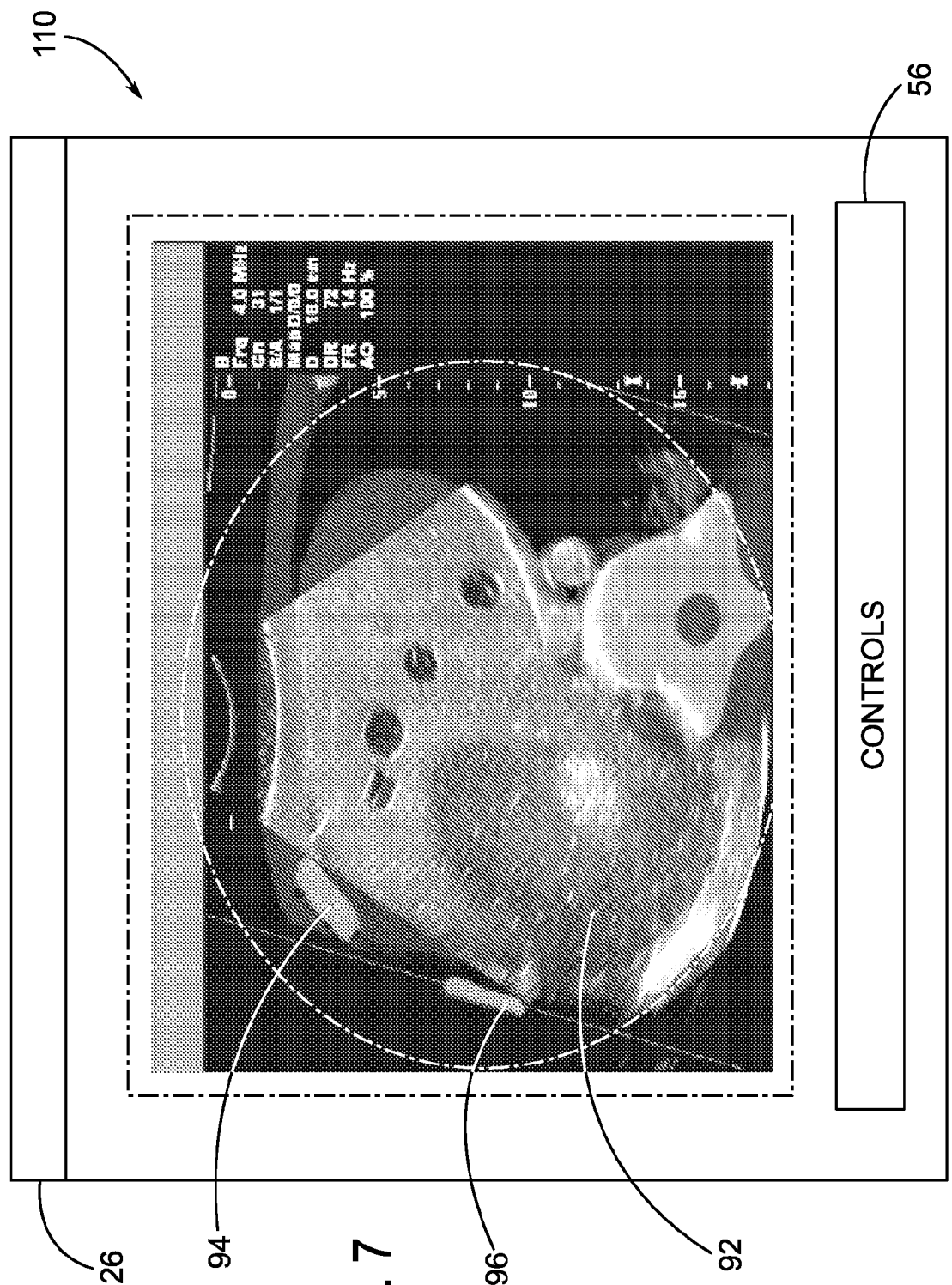
FIG. 7 is a front view of a display area of the exemplary diagnostic system of FIG. 1 depicting a method of visualizing a registered image in a simultaneous overlay configuration, in accordance with aspects of the present technique.

Combining the overlay viewing with the side-by-side viewing is dependent upon available screen space on the display. In other words, due to space constraints on the display, the simultaneous display of the combined image and the corresponding matching image slice unfortunately results in the images being partially clipped, displayed in a relatively small size, or both. As will be appreciated, the combined image includes information from the ultrasound image and the corresponding matching image slice in the pre-acquired image volume. This disadvantage may be overcome in accordance with aspects of the present technique. More particularly, in accordance with aspects of the present technique, only the overlaid combined image may be displayed on the entire screen space of the display 26, thereby facilitating the display of an unclipped overlaid combined image. Additionally, the overlaid image may be displayed at a substantially larger size. FIG. 7 illustrates a front view 110 of a display, such as the display 26 (see FIG. 1). More particularly, yet another method of visualizing a registered ultrasound image, in accordance with further aspects of the present technique, is depicted. Accordingly, a combined image, such as the combined image 96 (see FIG. 6) may be displayed on the entire screen of the display 26. As previously noted, the combined image 96 includes a color overlay 94 (see FIG. 6) overlaid on the ultrasound image 92 (see FIG. 6).

In accordance with further aspects of the present technique, a control may be provided on the system 10 (see FIG. 1), where the control may be configured to allow the clinician to switch between visualizing the 2D ultrasound image only, the matching image slice in the 3D pre-acquired image volume only, or a desired mix of the 2D ultrasound image and the matching image slice in the pre-acquired image volume. The working of this control may be better understood with reference to FIGS. 8-10.

Figure 8:
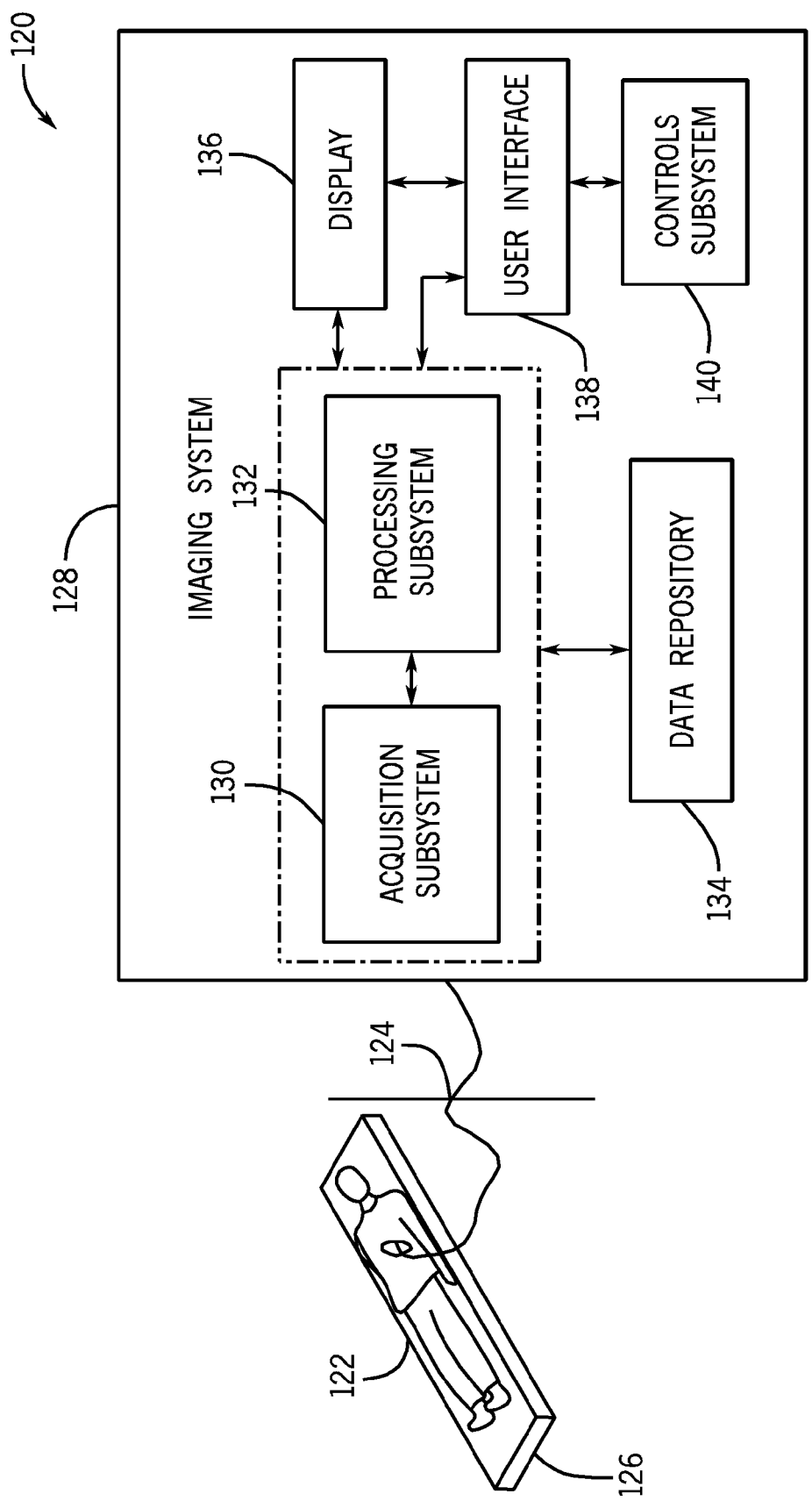
FIG. 8 is a block diagram of a physical implementation of an imaging system configured for use in the exemplary diagnostic system of FIG. 1.

Turning now to FIG. 8, a block diagram 120 illustrating an image acquisition system configured for use in the diagnostic system 10 (see FIG. 1) is depicted. The system 120 may be configured to acquire image data from a patient 122 via an image acquisition device 124. Reference numeral 126 may be representative of a table configured to aid in positioning the patient 122 for an imaging session. In one embodiment, the image acquisition device 124 may include a probe, where the probe may include an invasive probe, or a non-invasive or external probe, such as an external ultrasound probe, that is configured to aid in the acquisition of image data. Also, in certain other embodiments, image data may be acquired via one or more sensors (not shown in FIG. 8) that may be disposed on the patient 122. By way of example, the sensors may include physiological sensors (not shown) such as electrocardiogram (ECG) sensors and/or positional sensors such as electromagnetic field sensors or inertial sensors. These sensors may be operationally coupled to a data acquisition device, such as an imaging system, via leads (not shown in FIG. 8), for example.

The system 120 may also include an image acquisition system 128, such as, but not limited to, a medical imaging system that is in operative association with the image acquisition device 124. In one embodiment, the medical imaging system 128 may include an ultrasound imaging system. It should be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Additionally, the exemplary embodiments illustrated and described hereinafter may find application in multi-modality imaging systems that employ ultrasound imaging in conjunction with other imaging modalities, position-tracking systems or other sensor systems. Furthermore, it should be noted that although the exemplary embodiments illustrated hereinafter are described in the context of a medical imaging system, such as, but not limited to, an ultrasound imaging system, an optical imaging system, a CT imaging system, a MR imaging system, an X-ray imaging system, or a PET imaging system, or a combination thereof, other imaging systems, such as, but not limited to, a pipeline inspection system, a liquid reactor inspection system, a manufacturing inspection system, or other imaging systems are also contemplated in accordance with aspects of the present technique.

In a presently contemplated configuration, the medical imaging system 128 may include an acquisition subsystem 130 and a processing subsystem 132. Further, the acquisition subsystem 130 of the medical imaging system 128 may be configured to acquire image data representative of one or more anatomical regions of interest in the patient 122 via the image acquisition device 124. The image data acquired from the patient 122 may then be processed by the processing subsystem 132.

Additionally, the image data acquired and/or processed by the medical imaging system 128 may be employed to aid a clinician in identifying disease states, assessing need for treatment, determining suitable treatment options, guiding an interventional procedure, and/or monitoring the effect of treatment on the disease states. In certain embodiments, the processing subsystem 132 may be further coupled to a storage system, such as a data repository 134, where the data repository 134 is configured to receive image data.

Further, as illustrated in FIG. 8, the medical imaging system 128 may include a display 136 and a user interface 138. However, in certain embodiments, such as in a touch screen, the display 136 and the user interface 138 may overlap. Also, in some embodiments, the display 136 and the user interface 138 may include a common area. It may be noted that the display may include the display 26 (see FIG. 1). Additionally, the user interface 138 may include the operator console 24 (see FIG. 1). In accordance with aspects of the present technique, the display 136 of the medical imaging system 128 may be configured to display an image generated by the medical imaging system 128 based on the image data acquired via the image acquisition device 124. Additionally, the display 136 may also be configured to display a pre-acquired image volume, such as the reference image data set 52 (see FIG. 2). The display 136 may also be configured to facilitate visualization of a registered image, such as the registered image 34 (see FIG. 2).

In addition, the user interface 138 of the medical imaging system 128 may include a human interface device (not shown) configured to facilitate the clinician in manipulating image data displayed on the display 136. The human interface device may include a mouse-type device, a trackball, a joystick, a stylus, or a touch screen configured to facilitate the clinician to identify the one or more regions of interest. However, as will be appreciated, other human interface devices, such as, but not limited to, a touch screen, may also be employed. Furthermore, in accordance with aspects of the present technique, the user interface 138 may be configured to aid the clinician in navigating through the images acquired by the medical imaging system 128. Additionally, the user interface 138 may also be configured to aid in facilitating the visualization of the registered ultrasound image and the corresponding pre-acquired image volume or the matching image slice in the pre-acquired image volume, for example.

In accordance with aspects of the present technique, the imaging system 128 may include a controls subsystem 140 configured to allow the clinician to switch between visualizing the 2D ultrasound image only, the pre-acquired image volume, or a desired mix of the 2D image and pre-acquired image volume. It may be noted that the visualization of the images may include visualizing the entire pre-acquired image volume or at least a portion of the pre-acquired image volume. The at least a portion of the pre-acquired image volume may include a matching image slice in the 3D pre-acquired image volume, where the matching image slice corresponds to the ultrasound image.

With continuing reference to FIG. 8, in a presently contemplated configuration, the controls subsystem 140 is illustrated as being operatively coupled to the user interface 138. In the present example, the clinician may manipulate the controls subsystem 140 via use of the user interface 138.

Figure 9:
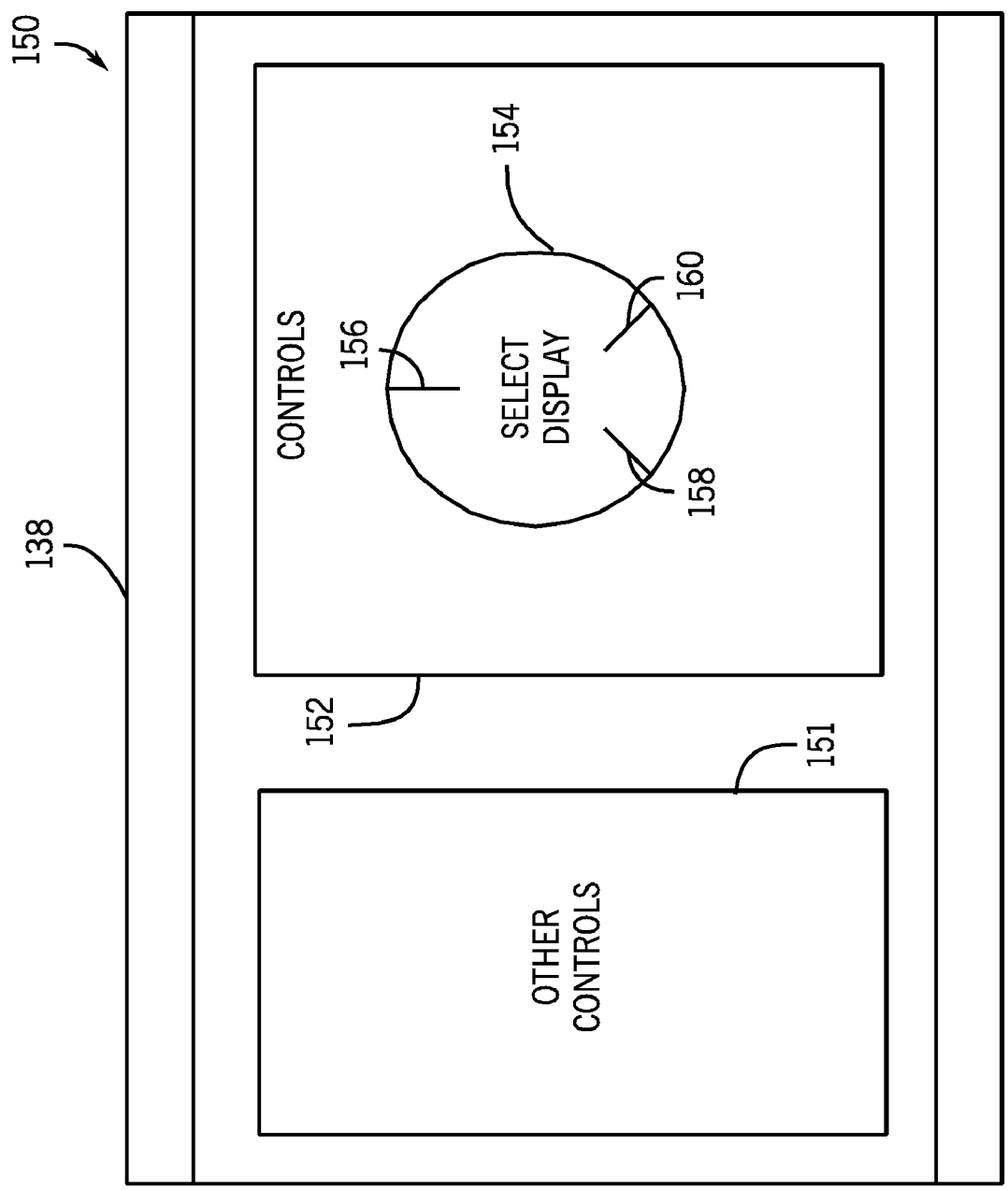
FIG. 9 is a front view of one embodiment of a user interface area of the exemplary diagnostic system of FIG. 1, in accordance with aspects of the present technique.

FIG. 9 depicts a front view 150 of the user interface 138 (see FIG. 8). In the present example, the user interface 138 may include other controls 151. The user interface 138 may also include controls 152 that are configured to allow the clinician to operate the controls subsystem 140. By way of example, the controls 152 may include a rotary control 154. In a presently contemplated configuration, the rotary control 154 may be configured to aid the clinician in switching between viewing the 2D ultrasound image only, viewing the 3D pre-acquired image volume only, or viewing a desired mix of the 2D image and the pre-acquired image volume.

In a presently contemplated configuration, the rotary control 154 may be configured to include three positional settings, where the positional settings may be configured to corresponding to one of a viewing the 2D ultrasound image only, viewing the 3D pre-acquired image volume only, or viewing a desired mix of the 2D image and the pre-acquired image volume. Accordingly, the rotary control 154 may be configured to include a first positional setting 156, a second positional setting 158 and a third positional setting 160. If the clinician positions the rotary control 154 at the first positional setting 156, then the medical imaging system 128 (see FIG. 8) may be configured to display only the 2D registered ultrasound image. Further, the medical imaging system 128 may be configured to display only the pre-acquired image volume or at least a portion of the pre-acquired image volume, such as, but not limited to, a matching image slice, if the clinician positions the rotary control 154 in the second positional setting 158. In addition, if the clinician positions the rotary control 154 in the third positional setting 160, the medical imaging system 128 may be configured to display a desired mix of the ultrasound image and the matching image slice in the pre-acquired image volume. By implementing the rotary control 154 as described hereinabove, the clinician may effortlessly cycle through the three display settings.

Alternatively, in accordance with further aspects of the present technique, the rotary control 154 may also be configured to be pushed and/or turned. Pushing the rotary control 154 may be configured to cycle the system 10 between viewing the 2D ultrasound image only, viewing the 3D pre-acquired image volume only, or viewing a desired mix of the 2D image and the pre-acquired image volume. Furthermore, when the rotary control 154 is positioned in the viewing a desired mix of the 2D image and the pre-acquired image volume position, then turning the rotary control 154 may be configured to provide an adjustment of a desired mixing of the ultrasound image and the pre-acquired image volume in the combined image.

Figure 10:
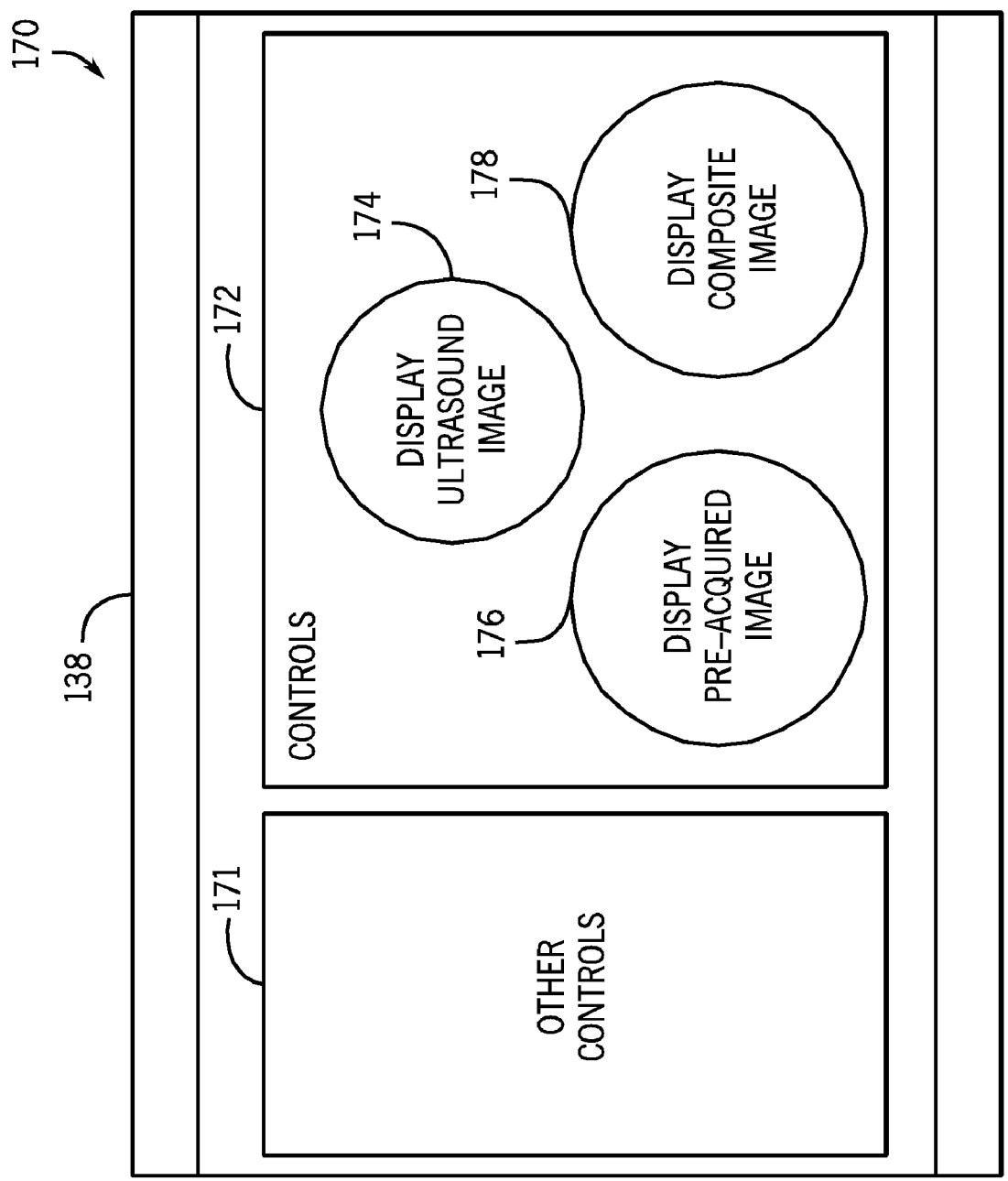
FIG. 10 is a front view of another embodiment of a user interface area of the exemplary diagnostic system of FIG. 1, in accordance with aspects of the present technique.

In another embodiment, the user interface 138 may include three separate controls to allow the clinician to switch between viewing the three images. Referring now to FIG. 10, a front view 170 of another embodiment of the user interface 138 (see FIG. 8) is illustrated. The user interface 138 is shown as including other controls 171. Further, the user interface 138 may also include controls 172 that are configured to allow the clinician to operate the controls subsystem 140. By way of example, in the embodiment illustrated in FIG. 10, the controls subsystem 140 is shown as including three separate buttons to allow the clinician to switch between viewing the 2D ultrasound image only, viewing the 3D pre-acquired image volume only, or viewing a desired mix of the 2D image and the matching image slice in the pre-acquired image volume. Accordingly, in the present example, if a display of only the 2D ultrasound image is desired, then the clinician may select a display ultrasound image button 174. Similarly, if a display of only the matching image slice is desired, then the clinician may select a display pre-acquired image button 176. However, if a display of a desired mix of the ultrasound image and pre-acquired image volume is desired, then the clinician may select a display composite image button 178. Here again, by implementing the controls 172 as described hereinabove, the clinician may effortlessly switch between the various displays by selecting one of the three buttons 174, 176, 178.

As described hereinabove with reference to FIGS. 9-10, the clinician may switch between viewing the 2D ultrasound image only, viewing the 3D pre-acquired image volume only, or viewing a desired mix of the 2D image and the matching image slice in the pre-acquired image volume. In accordance with yet another aspect of the present technique, a method of facilitating the generation of the desired mix of the 2D ultrasound image and the corresponding matching image slice is presented.

As will be appreciated, the design of a method configured to generate a composite image representative of a desired mix of the 2D ultrasound image and the pre-acquired image volume is of paramount significance as the acceptance of the display of a single overlaid composite image versus the simultaneous side-by-side display of the ultrasound image and the corresponding pre-acquired image volume may be dependent upon the quality of the composite image. In accordance with aspects of the present technique, a method for generating the composite image is presented. More particularly, the clinician may be allowed to select an intensity range of image data from the pre-acquired image volume to be mixed with the ultrasound image to generate the composite image. In one embodiment, the clinician may use a simple control to choose an absolute intensity of the pre-acquired image volume. Additionally, the clinician may also specify a lower threshold T1 and an upper threshold T2. Subsequently, the clinician may specify if an intensity between the two thresholds T1, T2 or an intensity outside the two thresholds T1, T2 is to be mixed with the ultrasound image to generate the composite image. The system 10 may be configured to allow the clinician control of these thresholds. Furthermore, the system 10 may also be configured to view the portion of the image data in the pre-acquired image volume that satisfies the thresholds and consequently be mixed with the ultrasound image data. Moreover, in accordance with further aspects of the present technique, similar thresholds may also be applied to the ultrasound image instead of or in addition to the thresholds on the pre-acquired image volume.

Figure 11:
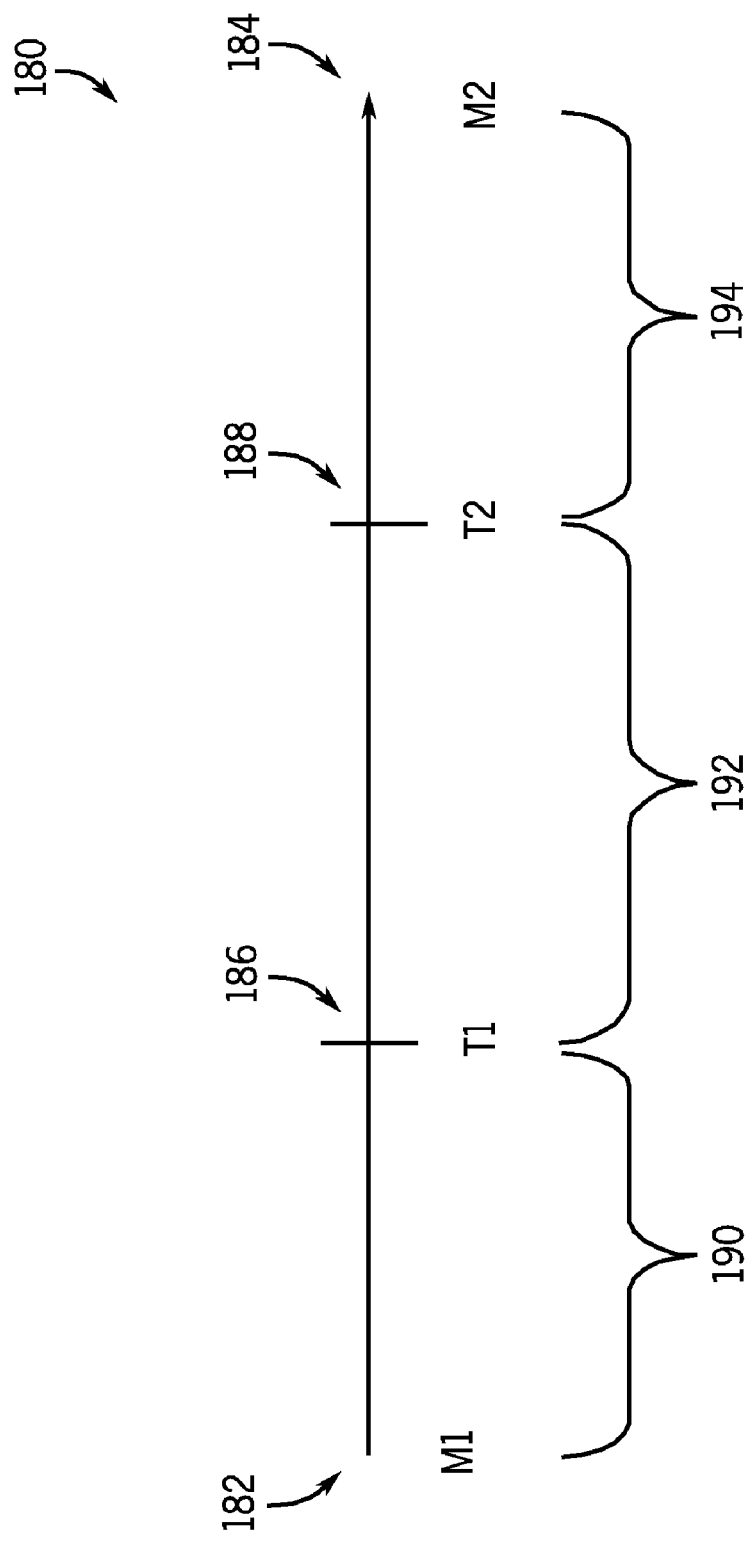
FIG. 11 is a diagrammatic illustration of an exemplary process of combining images for display, in accordance with aspects of the present technique.

The method of generating the composite image may be better understood with reference to FIG. 11. FIG. 11 illustrates a diagrammatic illustration 180 of the method of generating the composite image, such as the composite image 96 (see FIG. 7). The pre-acquired image volume may have a minimum intensity M1 182 and a maximum intensity of M2 184. Consequently, the pre-acquired image volume has an intensity in a range from about M1 to about M2. According to aspects of the present technique, the clinician may be configured to sub-divide this range M1→M2 into a plurality of sub-ranges by selecting two or more thresholds in the range. By way of example, the user may select a lower threshold T1 186 and an upper threshold T2 188. Consequently, the range M1→M2 may be sub-divided into three sub-ranges. A first sub-range M1→T1 may be represented by reference numeral 190, while reference numeral 192 may be indicative of a second sub-range T1→T2. Also, a third sub-range T2→M2 may generally be represented by reference numeral 194. It may be noted that each of these sub-ranges may be controlled via use of separate controls on the user interface 138 (see FIGS. 9-10), for example. These controls may be configured to facilitate generating a desired mix by combining of the 2D ultrasound image and the pre-acquired image volume. It may be noted that although in the present example the range M1→M2 is sub-divided into three sub-ranges, it will be understood that other number of sub-ranges are also envisaged in accordance with aspects of the present technique.

As noted hereinabove, the system 10 may be configured to allow the clinician to select image data either within a given sub-range or outside the given sub-range to be mixed with the ultrasound image. For example, if the clinician selects the first sub-range M1→T1 190, then the system 10 may be configured to mix about 0% of image data from the pre-acquired image volume having an intensity corresponding to this first sub-range 190 with about 100% of the ultrasound image data to generate the composite image. However, if the sub-range selected by the clinician includes the second sub-range T1→T2 192, then the system 10 may be configured to mix about 50% of image data in the pre-acquired image volume having an intensity corresponding to this second sub-range 192 with about 50% of the ultrasound image data to generate the composite image. Also, if the clinician selects the third sub-range T2→M2 194, then the system 10 may be configured to mix 100% of image data in the pre-acquired image volume having an intensity corresponding to this third sub-range 194 with about 0% of the ultrasound data to generate the composite image.

By implementing the method of generating the composite image as described hereinabove, a substantially superior combination of the ultrasound image and the pre-acquired image volume may be obtained. Also, the system 10 may be configured to allow the clinician to specify a combination of the ultrasound image and the pre-acquired image volume and accordingly adjust the mix.

In accordance with aspects of the present technique, another example of generating the composite image, such as the composite image 96 (see FIG. 7) is presented. With continuing reference to FIG. 11, the pre-acquired image volume may have a minimum intensity M1 182 and a maximum intensity of M2 184, and hence an intensity in a range from about M1 to about M2. This range M1→M2 is sub-divided into a plurality of sub-ranges (M1→T1 190, T2→M2 192, T2→M2 194) by selecting two or more thresholds in the range, as previously noted.

As noted hereinabove, the system 10 may be configured to allow the clinician to select image data either within a given sub-range or outside the given sub-range to be mixed with the ultrasound image. In a present example, at the point M1 182, the system may be configured to mix about 0% of image data from the pre-acquired image volume with about 100% of the ultrasound image data to generate the composite image. In addition, at point T1 186, the system 10 may be configured to mix about 50% of image data from the pre-acquired image volume with about 50% of the ultrasound image data to generate the composite image. Furthermore, for points in between M1 182 and T1 186, the combination may include a linear combination. For example, at point (T1−M1)/2 the system 10 may be configured to mix about 25% of image data in the pre-acquired image volume with about 75% of the ultrasound image data to generate the composite image. Also, at point T2 188, the system 10 may be configured to mix about 50% of image data from the pre-acquired image volume with about 50% of the ultrasound image data to generate the composite image, while at the point M2 184, the system 10 may be configured to mix about 100% of image data from the pre-acquired image volume with about 0% of the ultrasound image data to generate the composite image. Other examples may include at point T2+(M2−T2)/2, the system 10 may be configured to mix about 62.5% of image data from the pre-acquired image volume with about 37.5% of the ultrasound image data to generate the composite image.

As will be appreciated by those of ordinary skill in the art, the foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code, as will be appreciated by those of ordinary skill in the art, may be stored or adapted for storage on one or more tangible, machine readable media, such as on memory chips, local or remote hard disks, optical disks (that is, CD's or DVD's), or other media, which may be accessed by a processor-based system to execute the stored code. Note that the tangible media may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

The method of visualizing a registered ultrasound image and a corresponding pre-acquired image volume and the system for visualizing a registered image and a corresponding pre-acquired image volume described hereinabove dramatically simplify procedural workflow for imaging an anatomical region of interest in the patient. Using the various methods of visualizing the registered ultrasound image with the corresponding pre-acquired image volume or the corresponding image slice in the pre-acquired image volume advantageously allows the clinician to simultaneously view the two images, while overcoming the limitations of the presently available techniques where the side-by-side display of the two images is limited by the screen size or one of the two images require partial clipping. In addition by employing the techniques described hereinabove, a substantially enhanced anatomical context may be provided to the ultrasound image, thereby facilitating increased diagnostic confidence.

The description hereinabove of the embodiments of the methods for visualizing a registered image and the system have the technical effect of efficiently visualizing a registered ultrasound image and a corresponding pre-acquired image volume data set in a side-by-side configuration, thereby enhancing clinical workflow and facilitating superior diagnosis.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for visualizing a registered image, the method comprising:
   receiving a first image data set and at least one other image data set;
   displaying at least a portion of the first image data set on a first portion of a display;
   displaying at least a portion of the at least one other image data set on a second portion of the display; and
   selectively adjusting display of the at least a portion of the at least one other image data to provide a context to the first image data set.

2. The method of claim 1, wherein the first image data set is registered with the at least one other image data set.

3. The method of claim 1, wherein the first image data set is acquired via an ultrasound imaging system, and wherein the at least one other image data set comprises a pre-acquired image volume data set acquired via an imaging system.

4. The method of claim 1, wherein displaying at least a portion of the at least one other image data set comprises selecting a portion of the at least one other image data set that is substantially similar to the first image data set.

5. The method of claim 1, further comprising:
   displaying the at least one other image data set in a predetermined orientation on the second portion of the display; and
   extracting a matching image plane in the at least one other image data set, wherein the matching image plane corresponds to the first image data set.

6. The method of claim 5, further comprising displaying the at least one other image data set on the second portion of the display such that the matching image plane is substantially parallel to the display.

7. The method of claim 1, further comprising providing anatomical context information via use of one or more image planes in the at least one other image data set.

8. The method of claim 7, wherein the one or more image planes comprise one or more parallel planes in the at least one other image data set.

9. The method of claim 1, further comprising displaying a volume rendering of at least a portion of the at least one other image data set on the second portion of the display.

10. The method of claim 1, further comprising overlaying color image data on the first image data set, the at least one other image data set, or both.

11. The method of claim 1, further comprising:
    receiving a first plurality of image planes representative of the first image data set;
    displaying the first plurality of image planes in the first image data set on the first portion of the display; and
    displaying a second plurality of image planes in the at least one other image data set on the second portion of the display, wherein the second plurality of image planes comprises image planes in the at least one other image data set corresponding to the first plurality of image planes in the first image data set.

12. The method of claim 1, further comprising:
    obtaining a matching image plane in the at least one other image data set, wherein the matching image plane corresponds to the first image data set;
    incorporating information associated with the matching image plane in the first image data set to generate an embedded first image data set; and
    displaying the embedded first image data set on the first portion of the display.

13. The method of claim 1, further comprising:
    overlaying the first image data set on the at least one other image data set to generate a combined image; and
    selectively displaying the first image data set, the combined image, or both on predetermined portions of the display.

14. The method of claim 13, wherein selectively displaying the first image data set, the combined image, or both on predetermined portions of the display comprises:
    displaying the first image data set on the first portion of the display; and
    displaying the combined image on the second portion of the display.

15. The method of claim 14, further comprising displaying the combined image on the display of the imaging system.

16. The method of claim 1, further comprising generating a composite image by combining the first image data set and the at least one other image data set.

17. The method of claim 16, wherein generating a composite image comprises adjusting a combination of the first image data set and the at least one other image data set to generate the composite image.

18. The method of claim 17, wherein adjusting a combination comprises:
    identifying a range of intensities of the image data in the at least one other image data set;
    dividing the range of intensities into a plurality of sub-ranges; and
    selecting image data within a sub-range or outside a sub-range to be combined with the first image data set to generate the composite image.

19. The method of claim 16, further comprising cycling through a plurality of views of the first image data set, the at least one other image data set, the composite image, or a combination thereof.

20. A computer readable medium comprising one or more tangible media, wherein the one or more tangible media comprise:
    code adapted to receive a first image data set and at least one other image data set;
    code adapted to display at least a portion of the first image data set on a first portion of a display;
    code adapted to display at least a portion of the at least one other image data set on a second portion of the display; and code adapted to selectively adjusting display of the at least a portion of the at least one other image data to provide a context to the first image data set.

21. A method for visualizing a registered image, the method comprising:
receiving a first image data set and at least one other image data set, wherein the first image data set comprises an ultrasound image data set, and wherein the at least one other image data set comprises a pre-acquired medical image data set;
displaying at least a portion of the first image data set on a first portion of a display;
displaying at least a portion of the at least one other image data set on a second portion of the display; and
selectively adjusting display of the at least a portion of the at least one other image data to provide a context to the first image data set.

22. A system, comprising:
at least one imaging system configured to obtain a first image data set and at least one other image data set;
a processing sub-system operationally coupled to the at least one imaging system and comprising a visualization platform configured to:
display at least a portion of the first image data set on a first portion of a display;
display at least a portion of the at least one other image data set on a second portion of the display; and
selectively adjust display of the at least a portion of the at least one other image data to provide a context to the first image data set.

23. The system of claim 22, further comprising a controls subsystem, configured to combine the first image data set and the at least one other image data set to generate a composite image.

24. The system of claim 23, wherein the controls subsystem is configured to generate the composite image by adjusting a combination of the first image data set and the at least one other image data set.

25. The method of claim 24, where in the controls subsystem is further configured to cycle through a plurality of views of the first image data set, the at least one other image data set, the composite image, or a combination thereof.

* * * * *